(12) United States Patent
Negishi et al.

(10) Patent No.: US 9,133,121 B2
(45) Date of Patent: *Sep. 15, 2015

(54) WEAKLY BASIC HINDERED AMINES COMPOUNDS HAVING CARBONATE SKELETONS, SYNTHETIC RESIN COMPOSITIONS AND COATING COMPOSITIONS

(76) Inventors: Yoshinori Negishi, Saitama (JP); Takashi Ayabe, Saitama (JP); Etsuo Tobita, Saitama (JP)

(*) Notice: Subject to any disclaimer, the term of this patent is extended or adjusted under 35 U.S.C. 154(b) by 243 days.

This patent is subject to a terminal disclaimer.

(21) Appl. No.: 13/613,807

(22) Filed: Sep. 13, 2012

(65) Prior Publication Data

US 2013/0023611 A1    Jan. 24, 2013

Related U.S. Application Data

(62) Division of application No. 12/753,439, filed on Apr. 2, 2010, now Pat. No. 8,329,787, which is a division of application No. 10/591,533, filed as application No. PCT/JP2005/003807 on Feb. 28, 2005, now abandoned.

(30) Foreign Application Priority Data

Mar. 2, 2004   (JP) .................................. 2004-057297

(51) Int. Cl.
*C08K 5/3435*      (2006.01)
*C07D 211/94*      (2006.01)

(52) U.S. Cl.
CPC .......... *C07D 211/94* (2013.01); *C08K 5/3435* (2013.01)

(58) Field of Classification Search
CPC ........................... C08K 5/3435; C07D 211/94
USPC .......................................................... 524/99
See application file for complete search history.

(56) References Cited

U.S. PATENT DOCUMENTS

| | | | |
|---|---|---|---|
| 4,351,915 A | 9/1982 | Kubota et al. | |
| 5,124,378 A | 6/1992 | Behrens et al. | |
| 7,018,570 B2 | 3/2006 | Haruna et al. | |
| 8,034,856 B2 | 10/2011 | Mizokawa et al. | |
| 8,293,824 B2* | 10/2012 | Negishi et al. | 524/102 |
| 8,329,787 B2* | 12/2012 | Negishi et al. | 524/99 |
| 2003/0088000 A1 | 5/2003 | Kimura et al. | |
| 2004/0122137 A1* | 6/2004 | Haruna et al. | 524/89 |
| 2010/0249288 A1 | 9/2010 | Mizokawa et al. | |
| 2011/0015307 A1 | 1/2011 | Fukushima et al. | |
| 2011/0028611 A1 | 2/2011 | Mizokawa et al. | |
| 2012/0247559 A1* | 10/2012 | Nakamura et al. | 136/259 |

FOREIGN PATENT DOCUMENTS

| | | |
|---|---|---|
| JP | 2001/210365 A | 5/2001 |
| WO | WO-02/100970 | 10/2002 |

OTHER PUBLICATIONS

English language machine translation of JP 2001-210365, Aug. 3, 2001.*
Xu et al., "Journal of the Electrochemical Society", 2001, vol. 149, No. (5), pp. A622-A626.

* cited by examiner

*Primary Examiner* — Angela C Scott
(74) *Attorney, Agent, or Firm* — Mullen, White, Zelano, Branigan, P.C.

(57) ABSTRACT

Hindered amines represented by the general formula (I): (wherein R is an alkyl or hydroxyalkyl group having 1 to 30 carbon atoms or alkenyl having 2 to 30 carbon atoms; n is an integer of 1 to 4; when n is 1, $R^1$ is alkyl having 1 to 22 carbon atoms, alkenyl having 2 to 22 carbon atoms, or a group represented by the general formula (III): (R is as defined above), while when n is 2 to 4, $R^1$ is an n-valent organic group having 2 to 20 carbon atoms). When added to synthetic resins or coating materials, the amines can impart long-period stabilizing effect to the resins or the materials and exhibit excellent resistance to extraction with acid rain or chemicals.

13 Claims, No Drawings

WEAKLY BASIC HINDERED AMINES COMPOUNDS HAVING CARBONATE SKELETONS, SYNTHETIC RESIN COMPOSITIONS AND COATING COMPOSITIONS

FIELD OF THE INVENTION

The present invention relates to weakly basic hindered amine compounds having carbonate skeletons.

BACKGROUND ART

Hindered amine compounds are known to suppress the photodegradation of organic substances such as synthetic resins, and since the stabilization effect is different depending on the structure of the amine and the environment in which it is used, amines with active hydrogen atoms, amines without active hydrogen atoms and alkyloxyamines which are even more weakly basic than tertiary amines, have been considered for this purpose. The idea of introducing a triazine skeleton in order to enhance compatibility with the synthetic resin to be stabilized or its extraction resistance, has also been considered.

For example, prior art hindered amine compounds, when used with polyolefin resins, had low compatibility with the resin, and since they vaporized from the resin, they had the problem that their stabilization effect did not endure. Moreover, in applications where they came in contact with acid rain and agricultural chemicals, there was also the problem that they were extracted by the acid.

Hindered amine compounds having a carbonate structure have been proposed in Tokkai-Sho 62-273239 (claims and compounds No. 30, No. 31), Tokkai-Sho 63-75019 (claims and compounds I-19, I-20, I-21), for the purpose of stabilizing polyolefin resins or as a catalyst quencher in the manufacture of oxymethylene (co)polymers.

However, there is neither any disclosure nor suggestion of weakly basic hindered amine compounds having an alkyloxyamine structure.

As an example of a weakly basic hindered amine compound, a compound having such an alkyloxyamine structure is proposed in Tokko-Sho 49-40557 (claims), and weakly basic hindered amine compounds having various skeletons are proposed in Tokkai-Hei 1-113368 (claims), e.g., hindered amines having a carboxylate structure, amide structure, carbamate structure or acetal structure.

Since weakly basic hindered amine compounds show superior resistance to acid extraction, their practical use in polyolefin agricultural films has been proposed, e.g., in Tokkai-Hei 2001-139821 (claims).

However, there is neither any disclosure nor suggestion of weakly basic hindered amine compounds having a carbonate structure.

Many hindered amine compounds have been proposed in the prior art, but for example in the case of agricultural films, since light transmissivity (which depends on the stability of the resin in the film) has a major impact on the growth of crops, a hindered amine compound which had a better longer-term stabilization effect was desired.

SUMMARY OF THE INVENTION

The present invention therefore proposes a hindered amine compound which confers long-term stabilization on synthetic resins, and which shows superior resistance to extraction by acid rain or chemicals.

The Inventors, as a result of extensive research carried out to resolve this problem, found that the hindered amine compound having a carbonate structure represented with by the general formula (I) or (II) gave excellent long-term stabilization of a synthetic resin, and thereby arrived at the present invention.

The first invention therefore provides a hindered amine compound represented by the general formula (I) or (II):

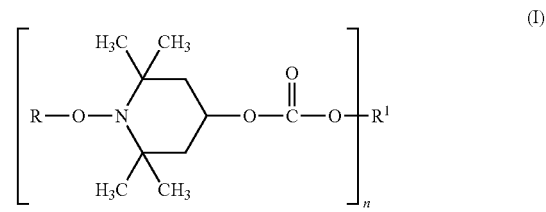

(in the formula, R is an alkyl group or a hydroxyalkyl group having 1-30 carbon atoms, or an alkenyl group having 2-30 carbon atoms, and n is an integer from 1-6. When n=1, $R^1$ is an alkyl group having 1-22 carbon atoms, an alkenyl group having 2-22 carbon atoms, or the group represented by the following general formula (III):

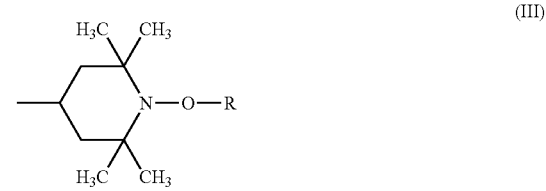

(R is the same alkyl group or hydroxyalkyl group having 1-30 carbon atoms, or alkenyl group having 2-30 carbon atoms as R above).

When n=2-6, $R^1$ is an organic group having 2-20 carbon atoms of valency n).

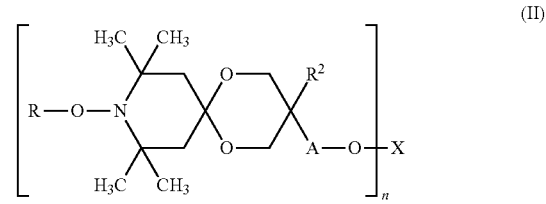

(in the formula, R is an alkyl group having 1-30 carbon atoms or an alkenyl group having 2-30 carbon atoms, $R^2$ is a hydrogen atom, an alkyl group having 1-22 carbon atoms or an alkenyl group having 2-22 carbon atoms, and A is a single bond, a linear- or branched-alkylene group having 1-12 carbon atoms or an alkylene group having ether linkage; n is an integer from 2-6; X is —C(═O)—, a linear- or branched-alkylene group having 4-40 carbon atoms with a terminal —C(═O)O—, a linear- or branched-alkylene group having 4-40 carbon atoms with a carbonic acid ester linkage, or an organic group having 6-30 carbon atoms with 3-6 terminal —O—C(═O)—).

The second invention provides the hindered amine compound of the first invention wherein, in the general formula (I), R is an alkyl group having 4-22 carbon atoms, n=2, and $R^1$ is an alkylene group having 2-12 carbon atoms.

The third invention provides the hindered amine compound of the first invention wherein, in the general formula (I), n=1, and $R^1$ is a group having the following general formula (III):

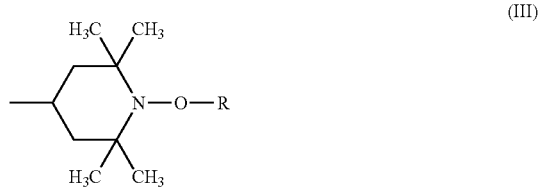

(R is an alkyl group having 10-22 carbon atoms).

The fourth invention provides a synthetic resin composition wherein 0.01-10 weight parts of the hindered amine compound according to any of the first-third inventions is blended with 100 weight parts of a synthetic resin.

The fifth invention provides a polyolefin resin composition wherein 0.05-5 weight parts of the hindered amine compounds according to any of the first-third inventions is blended with 100 weight parts of a polyolefin resin.

The sixth invention provides a polyolefin film for agricultural use comprising the polyolefin resin composition according to the fifth invention.

The seventh invention provides a coating composition stabilized by the hindered amine compound according to any of the first-third inventions.

The eighth invention provides a synthetic resin composition wherein 1-30 weight parts of one or more of melamine phosphate, melamine pyrophosphate, melamine polyphosphate, piperazine phosphate, piperazine pyrophosphate and piperazine polyphosphate as a flame retarder, and 0.01-10 weight parts of the hindered amine compound according to any of the first-third inventions, is blended with 100 weight parts of a synthetic resin.

DESCRIPTION OF THE PREFERRED EMBODIMENTS

Some preferred aspects of the invention will now be described.

The hindered amine compound of the present invention is a weakly basic hindered amine compound having a carbonate skeleton represented by the general formula (I) or (II).

Examples of an alkyl group having 1-30 carbon atoms represented by R in the general formulae (I) and (II), are linear- or branched-alkyl groups such as methyl, ethyl, propyl, isopropyl, butyl, isobutyl, sec-butyl, tert-butyl, pentyl, sec-pentyl, tert-pentyl, hexyl, heptyl, octyl, iso-octyl, 2-ethylhexyl, tert-octyl, nonyl, isononyl, decyl, undecyl, dodecyl, tridecyl, tetradecyl, pentadecyl, hexadecyl, heptadecyl and octadecyl, and cycloalkyl groups such as cyclohexyl.

Examples of a hydroxyalkyl group having 1-30 carbon atoms represented by R in the general formulae (I) and (II), are 2-hydroxyethyl, 2-hydroxypropyl, 2-hydroxybutyl and 2-hydroxy-2-methylpropyl.

R may be identical or different every n repeating units.

Examples of an alkenyl group having 2-30 carbon atoms represented by R in the general formulae (I) and (II) are alkenyl groups corresponding to the aforesaid alkyl groups such as vinyl, allyl, butenyl, pentenyl and oleyl.

In the general formula (I), when n=1, $R^1$ is an alkyl group having 1-22 carbon atoms, an alkenyl group having 2-22 carbon atoms, or a group having the aforesaid general formula (III).

In the general formula (I), when n=1, examples of an alkyl group having 1-22 carbon atoms represented by $R^1$ are methyl, ethyl, propyl, isopropyl, butyl, isobutyl, sec-butyl, tert-butyl, pentyl, sec-pentyl, tert-pentyl, hexyl, heptyl, octyl, iso-octyl, 2-ethylhexyl, tert-octyl, nonyl, isononyl, decyl, undecyl, dodecyl, tridecyl, tetradecyl, pentadecyl, hexadecyl, heptadecyl, octadecyl and behenyl.

In the general formula (I), when n=1, examples of an alkenyl group having 2-22 carbon atoms represented by $R^1$ are alkenyl groups corresponding to the aforesaid alkyl groups such as vinyl, allyl, butenyl, pentenyl and oleyl.

In the general formula (I), when n=1, and $R^1$ is a group having the aforesaid general formula (III), an example of R in the general formula (III) is identical to R in the general formula (I), but it may be identical to or different from R in the general formula (I).

R is preferably an alkyl group having 10-22 carbon atoms.

In the general formula (I), when n=2-6, examples of an organic group having 2-20 carbon atoms of valency n represented by $R^1$ are residues other than the hydroxyl group of a multivalent hydroxyl compound of valency n.

Examples of the aforesaid multivalent hydroxyl compound are ethylene glycol, propylene glycol, 1,3-propanediol, 1,2-butanediol, 1,3-butanediol, 1,4-butanediol, neopentylglycol, 1,6-hexanediol, 1,3-cyclohexanediol, 1,4-cyclohexanediol, bisphenol A hydrate, bisphenol F hydrate, diethylene glycol, triethylene glycol, glycerol, trimethylol propane, pentaerythritol, and dip entaerythritol.

In the general formula (II), $R^2$ is a hydrogen atom, an alkyl group having 1-22 carbon atoms, or an alkenyl group having 2-22 carbon atoms.

Examples of an alkyl group having 1-22 carbon atoms represented by $R^2$, are the alkyl groups in the aforesaid R having this number of carbon atoms.

Examples of an alkenyl group having 2-22 carbon atoms represented by $R^2$ in the general formula (II), are the alkenyl groups in the aforesaid R having this number of carbon atoms.

$R^2$ may be the same or may differ every n repeating units.

In the general formula (II), A represents a single bond, a linear- or branched-alkylene group having 1-12 carbon atoms, or an alkylene group with an ether linkage.

Examples of an alkylene group having 1-12 carbon atoms represented by A are methylene, 1,2-ethylene, 1,2-propylene, 1,3-propylene, tetramethylene, 1,2-butylene, 1,3-butylene, pentamethylene, 2,2-dimethyltrimethylene, hexamethylene and octamethylene.

Examples of a linear- or branched-alkylene group having 1-12 carbon atoms with an ether linkage represented by A in the general formula (II), are:

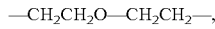

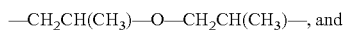

A may be the same or different every n repeating units (n=2-6).

In the general formula (II), X is —C(=O)—, a linear- or branched-alkylene group having 4-40 carbon atoms with a terminal —C(=O)O—, a linear- or branched-alkylene group having 4-40 carbon atoms with a carbonic acid ester linkage, or an organic group having 6-30 carbon atoms with 3-6 terminal —O—C(=O)—.

In the general formula (II), an example of an alkylene group having 4-40 carbon atoms with a terminal —C(=O)O— represented by X, is:

In the general formula (II), an example of an alkylene group having a carbonic acid ester linkage represented by X, is:

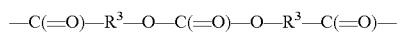

(where p is a number from 2-40, and $R^3$ is an alkylene group having 2-18 carbon atoms).

In the general formula (II), examples of an organic group having 3-6 terminal —O—C(=O)— represented by X, are:

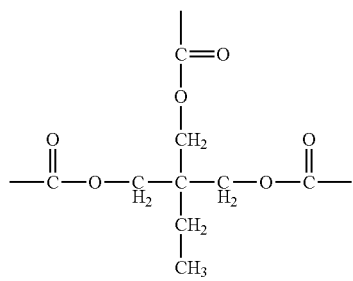

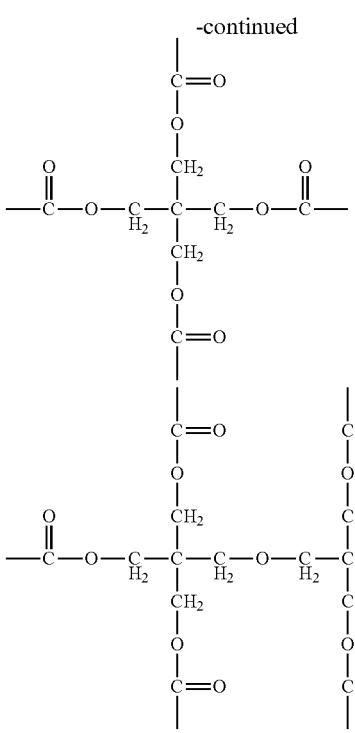

More specifically, examples of a compound represented by the general formula (I) are Compounds No. 1-No. 6 and Compound No. 13, and examples of a compound represented by the general formula (II) are Compounds No. 7-No. 12. However, the invention is not to be construed as being limited in any way by the following compounds:

(Compound No. 1)
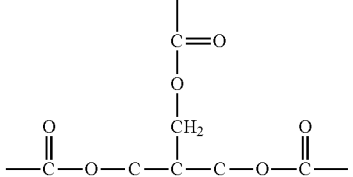

(Compound No. 2)
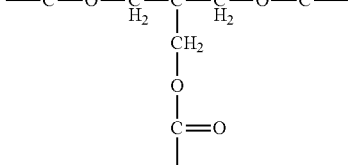

(Compound No. 3)
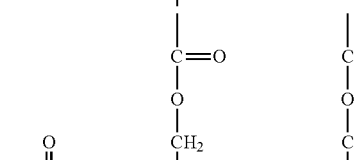

(Compound No. 4)
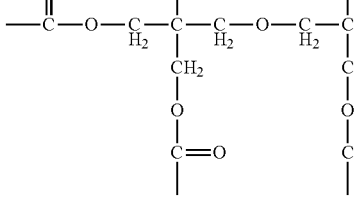

-continued
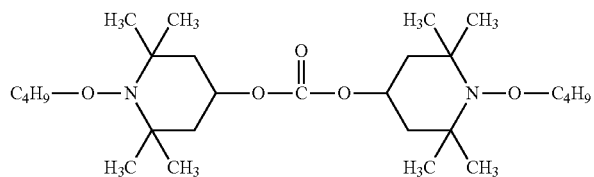
(Compound No. 5)
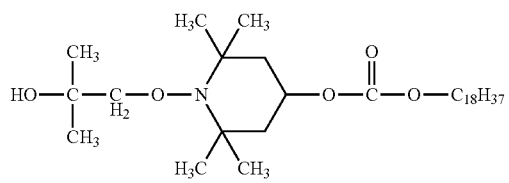
(Compound No. 6)
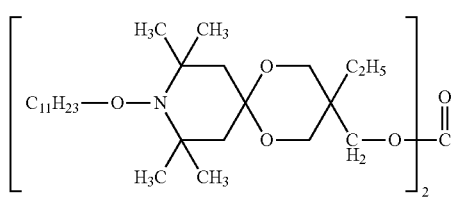
(Compound No. 7)
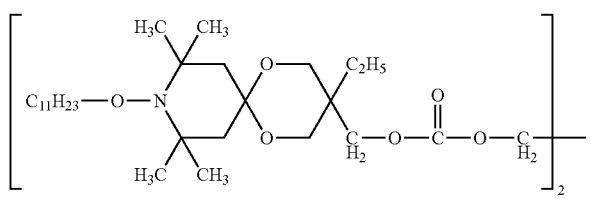
(Compound No. 8)
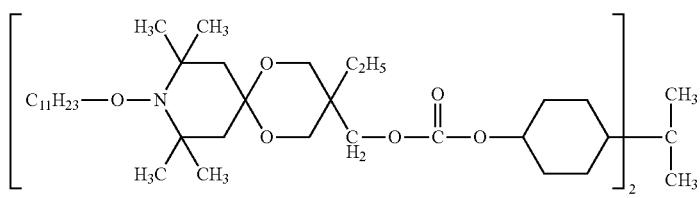
(Compound No. 9)
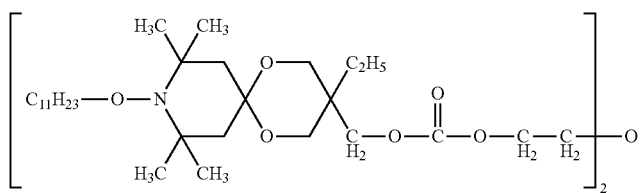
(Compound No. 10)
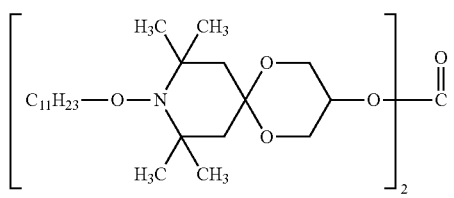
(Compound No. 11)
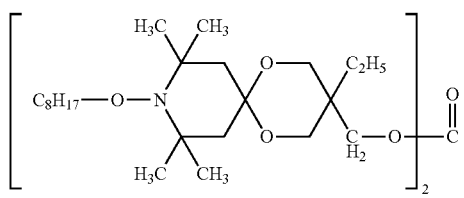
(Compound No. 12)

-continued

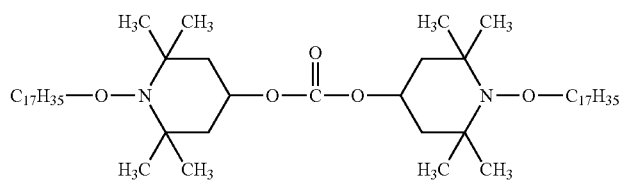

(Compound No. 13)

The method of synthesizing the compound represented by the general formula (I) is not particularly limited, but it may be synthesized by the methods usually used for organic synthesis shown in the Examples described later, and it may be purified by distillation, recrystallization, re-precipitation, a filter medium or an adsorbent as required.

Examples of the synthetic resin stabilized by the hindered amine compound represented by the general formula (I), are homopolymers or copolymers of α-olefins such as polypropylene, low density polyethylene, linear low density polyethylene, high density polyethylene, polybutene-1, poly-3-methylpentene, poly-4-methylpentene and ethylene-propylene copolymer; copolymers of α-olefins with polyunsaturated compounds such as conjugated dienes or unconjugated dienes; copolymers of α-olefins with acrylic acid, methacrylic acid, vinylacetate etc.; linear polyesters or acid-modified polyesters such as polyethylene terephthalate, polyethylene terephthalate isophthalate, polyethylene p-oxybenzoate and polybutylene terephthalate; aliphatic polyesters having biodegradability such as polylactic acid; polyamides such as polycaprolactam and polyhexamethylene adipamide; polyimides; polystyrenes and copolymers of styrene and/or α-methylstyrene with other monomers (e.g., maleic anhydride, phenyl maleimide, methyl methacrylate, butadiene, acrylonitrile) (e.g., AS resin, ABS resin, MBS resin, heat-resistant ABS resin); halogen containing resin such as polyvinyl chloride, polyvinylidene chloride, polyethylene chloride, polypropylene chloride, polyvinylidene fluoride, chlorinated rubber, vinyl chloride-vinyl acetate copolymer, vinyl chloride-ethylene copolymer, vinyl chloride-vinylidene chloride copolymer, vinyl chloride-vinylidene chloride-vinyl acetate terpolymer, vinyl chloride-acrylic ester copolymer, vinyl chloride-maleic acid ester copolymer and vinyl chloride-cyclohexyl maleimide copolymer; polymers of (meth)acrylic acid esters such as methyl(meth)acrylate, ethyl(meth)acrylate and octyl(meth)acrylate; polyether ketone, polyvinyl acetate, polyvinyl formal, polyvinyl butyral and polyvinyl alcohol; linear- or branched-polycarbonates, petroleum resin, cumarone resin, polyphenylene oxide, polyphenylene sulfide, polyurethane, thermoplastic resins such as cellulose resins; thermosetting resins such as epoxy resin, phenol resin, urea resin, melamine resin and unsaturated polyester resins; elastomers such as isoprene rubber, butadiene rubber, butadiene-styrene copolymer rubber, butadiene-acrylonitrile copolymer rubber, acrylonitrile-butadiene-styrene copolymer rubber, and copolymer rubbers with α-olefins such as ethylene, propylene and butane-1, and terpolymer rubbers of ethylene-α-olefins with unconjugated dienes such as ethylidene norbornene and cyclopentadiene; cyclo-olefin copolymers; and silicone resins. These resins and/or elastomers may be alloyed or blended together.

Preferably, it is a polyolefin resin.

The stabilizing effect on this synthetic resin differs according to the degree of stereoregularity, specific gravity, type of polymerization catalyst in the polyolefin such as a Ziegler-Natta catalyst or metallocene catalyst, whether or not the polymerization catalyst is removed and to what extent, degree of crystallization, polymerization conditions such as temperature and pressure, type of crystals, size of lamellar crystals measured by X-ray small angle scattering, the aspect ratio of crystals, solubility in aromatic or aliphatic solvents, solution viscosity, melt viscosity, average molecular weight, extent of molecular weight distribution, number of peaks in the molecular weight distribution, whether it is a block or random copolymer and the blending ratio of each monomer, but any of the aforesaid resins may be used.

The hindered amine compound of the invention is used for various shaping starting materials in a synthetic resin composition wherein 0.01-10 weight parts, and preferably 0.05-5 weight parts, is blended with 100 weight parts of the aforesaid synthetic resin.

If the blending amount of the hindered amine compound is too much below than the aforesaid range, there is no stabilization effect, whereas if it is too much above the aforesaid range, no additional effect can be expected and there is a risk that the physical properties of the resin will be impaired.

In particular, in the case of a polyolefin resin, 0.05-5 weight parts and preferably 0.1-3 weight parts of the hindered amine compound is blended with 100 weight parts of the polyolefin resin.

The method of blending the hindered amine compound represented by the general formula (1) is not particularly limited, and may be any technique for blending a stabilizer with a resin known in the art. For example, it may be added to the polymerization system before the synthetic resin is polymerized, added during polymerization, or added after polymerization. If it is to be added after polymerization, a powder of the resin, pellets or the mixture from a Henschel mixer may be kneaded in an extruder or the like, sprayed as a solution to impregnate the synthetic resin, or used after making up a master batch. The type of processing machine, processing temperature and cooling conditions after processing are not particularly limited, but the conditions are preferably selected so that the physical properties of the resin suit the envisaged application. The hindered amine compound of the invention may also be formed into particles, either alone or with another additive.

When using the hindered amine compound represented by the general formula (I) of the present invention for stabilizing a synthetic resin or coating material, various kinds of blending agents usually used for resins may be employed as required. Examples of such blending agents are a phenol type antioxidant, sulfur type antioxidant, phosphorus type antioxidant, ultraviolet absorber, another hindered amine compound, nucleating agent, flame retarder, flame retarder auxiliary agent, lubricant, filler, plasticizer, fibrous filler, metal soap, hydrotalcite, antistatic agent, pigment, dye, antibacterial agent, anti-mold agent, antiseptic, stain-proofing agent, anticorrosive, surfactant, compatibilizer, sedimentation inhibitor, polymerization inhibitor, thickener, defoaming agent, coupling agent, leveling agent, drying agent, anticreasing agent, dehydrating agent, curing catalyst, adhesion imparting agent and foaming agent.

Examples of a phenol type antioxidant are α-tocopherol, 2,6-di-t-butyl-p-cresol, 2,6-diphenyl-4-octadecyloxyphenol, distearyl(3,5-di-t-butyl-4-hydroxybenzyl)phosphonate, 1,6-hexamethylene bis[(3,5-di-t-butyl-4-hydroxyphenyl) propionic acid amide], 4,4'-thiobis(6-t-butyl-m-cresol), 2,2'-methylene bis(4-methyl-6-t-butylphenol), 2,2'-methylene bis(4-ethyl-6-t-butylphenol), 4,4'-butylidene bis(6-t-butyl-m-cresol), 2,2'-ethylidene bis(4,6-di-t-butylphenol), 2,2'-ethylidene bis(4-s-butyl-6-t-butylphenol), 1,1,3-tris(2-methyl-4-hydroxy-5-t-butylphenyl)butane, 1,3,5-tris(2,6-dimethyl-3-hydroxy-4-t-butylbenzyl)isocyanurate, 1,3,5-tris (3,5-di-t-butyl-4-hydroxybenzyl)isocyanurate, 1,3,5-tris(3, 5-di-t-butyl-4-hydroxybenzyl)-2,4,6-trimethylbenzene, 2-t-butyl-4-methyl-6-(2-acryloyloxy-3-t-butyl-5-methylbenzyl) phenol, stearyl(3,5-di-t-butyl-4-hydroxyphenyl) propionate, thiodiethyleneglycol bis[(3,5-di-t-butyl-4-hydroxyphenyl) propionate], 1,6-hexamethylene bis-(3,5-di-t-butyl-4-hydroxyphenyl)propionate], bis[3,3-bis(4-hydroxy-3-t-butylphenyl)butyric acid]glycolester, bis[2-t-butyl-4-methyl-6-(2-hydroxy-3-t-butyl-5-methylbenzyl)phenyl]terephthalate, 1,3,5-tris[(3,5-di-t-butyl-4-hydroxyphenyl)propionyl oxyethyl]isocyanurate, 3,9-bis[1,1-dimethyl-2{(3-t-butyl-4-hydroxy-5-methylphenyl)propionyloxy}ethyl]2,4,8,10-tetraoxaspiro[5.5]undecane and triethyleneglycol bis[(3-t-butyl-4-hydroxy-5-methylphenyl)propionate].

Examples of a sulfur type antioxidant are dialkyl thiodipropionates such as dilauryl thiodipropionate, dimyristyl thiodipropionate and distearyl thiodipropionate, and β-alkyl mercaptopropionic acid esters of polyols such as pentaerythritol tetra(β-dodecyl mercaptopropionate).

Examples of a phosphorus type antioxidant are tris-nonyl phenylphosphite, tris[2-t-butyl-4-(3-t-butyl-4-hydroxy-5-methylphenylthio)-5-methylphenyl]phosphite, tridecyl phosphite, octyl diphenyl phosphite, di(decyl)monophenyl phosphite, di(tridecyl)pentaerythritol diphosphite, di(nonylphenyl)pentaerythritol diphosphite, bis(2,4-di-t-butylphenyl)pentaerythritol diphosphite, bis(2,6-di-t-butyl-4-methylphenyl)pentaerythritol diphosphite, bis(2,4,6-tri-t-butylphenyl)pentaerythritol diphosphite, bis(2,4-dicumylphenyl)pentaerythritoldiphosphite, tetra(tridecyl) isopropylidene diphenoldiphosphite, tetra(tridecyl)-4,4'-n-butylidene bis(2-t-butyl-5-methylphenol)diphosphite, hexa (tridecyl)-1,1,3-tris(2-methyl-4-hydroxy-5-t-butylphenyl) butanetriphosphite, tetrakis(2,4-di-t-butylphenyl) biphenylene diphosphonite, 9,10-dihydro-9-oxa-10-phosphaphenanthrene-10-oxide, 2,2'-methylene bis(4,6-t-butylphenyl)-2-ethylhexylphosphite, 2,2'-methylene bis(4,6-t-butylphenyl)-octadecylphosphite, 2,2'-ethylidene bis(4,6-di-t-butylphenyl)fluorophosphite, tris(2-[(2,4,8,10-tetrakis-t-butyldibenzo[d,f][1,3,2]dioxaphosphepine-6-il)oxy]ethyl) amine, and the phosphites of 2-ethyl-2-butyl propyleneglycol and 2,4,6-tri-t-butylphenol.

The aforesaid phenol type, sulfur type and phosphorus type antioxidant may be used alone or together, in which case their total amount is 0.001-10 weight parts, or more preferably, 0.05-5 weight parts relative to 100 weight parts of resin.

Examples of an aforesaid ultraviolet absorber are 2-hydroxybenzophenones such as 2,4-dihydroxybenzophenone, 2-hydroxy-4-methoxybenzophenone, 2-hydroxy-4-octoxybenzophenone, 5,5'-methylene bis(2-hydroxy-4-methoxybenzophenone); 2-(2'-hydroxyphenyl)benzotriazoles such as 2-(2'-hydroxy-5'-methylphenyl)benzotriazole, 2-(2'-hydroxy-3',5'-di-t-butylphenyl)-5-chlorobenzotriazole, 2-(2'-hydroxy-3'-t-butyl-5'-methylphenyl)-5-chlorobenzotriazole, 2-(2'-hydroxy-5'-t-octylphenyl)benzotriazole, 2-(2'-hydroxy-3',5'-dicumylphenyl)benzotriazole and 2-(2'-hydroxy-3'-t-butyl-5'-carboxyphenyl)benzotriazole; benzoates such as phenyl salicylate, resorcinol monobenzoate, 2,4-di-t-butylphenyl-3,5-di-t-butyl-4-hydroxybenzoate, 2,4-di-t-amylphenyl-3,5-di-t-butyl-4-hydroxybenzoate and hexadecyl-3,5-di-t-butyl-4-hydroxybenzoate; substituted oxanilides such as 2-ethyl-2'-ethoxyoxanilide and 2-ethoxy-4'-dodecyloxanilide; cyanoacrylates such as ethyl-α-cyano-β, β-diphenylacrylate and methyl-2-cyano-3-methyl-3-(p-methoxyphenyl)acrylate; and triallyl triazines such as 2-(2-hydroxy-4-octoxyphenyl)-4,6-bis(2,4-di-t-butylphenyl)-s-triazine, 2-(2-hydroxy-4-methoxyphenyl)-4,6-diphenyl-s-triazine and 2-(2-hydroxy-4-propoxy-5-methylphenyl)-4,6-bis(2,4-di-t-butylphenyl)-s-triazine. These are used in the amount of 0.001-10 weight parts, but more preferably 0.05-5 weight parts, relative to 100 weight parts of resin.

Examples of the other hindered amine compound mentioned above, are 2,2,6,6-tetramethyl-4-piperidyl-1-oxy-, 2,2,6,6-tetramethyl-4-piperidyl stearate, 1,2,2,6,6-pentamethyl-4-piperidyl stearate, 2,2,6,6-tetramethyl-4-piperidyl benzoate, bis(2,2,6,6-tetramethyl-4-piperidyl)sebacate, bis (1,2,2,6,6-pentamethyl-4-piperidyl)sebacate, tetrakis(2,2,6, 6-tetra-methyl-4-piperidylbutane)tetracarboxylate, tetrakis (1,2,2,6,6-pentamethyl-4-piperidylbutane)tetracarboxylate, bis(2,2,6,6-tetramethyl-4-piperidyl)-di(tridecyl)-1,2,3,4-butanetetracarboxylate, bis(1,2,2,6,6-pentamethyl-4-piperidyl)-di(tridecyl)-1,2,3,4-butanetetracarboxylate, bis(1,2, 2,6,6-pentamethyl-4-piperidyl)-2-butyl-2-(3,5-di-t-butyl-4-hydroxybenzyl) malonate, 1-(2-hydroxyethyl)-2,2,6,6-tetramethyl-4-piperidinol/diethylsuccinate condensation polymer, 1,6-bis(2,2,6,6-tetramethyl-4-piperidylamino) hexane/dibromoethane condensation polymer, 1,6-bis(2,2,6,6-tetramethyl-4-piperidylamino) hexane/2,4-dichloro-6-morpholino-s-triazine condensation polymer, 1,6-bis(2,2,6,6-tetramethyl-4-piperidylamino) hexane/2,4-dichloro-6-t-octylamino-s-triazine condensation polymer, 1,5,8,12-tetrakis[2,4-bis(N-butyl-N-(2,2,6,6-tetramethyl-4-piperidyl) amino)-s-triazine-6-il]-1,5,8,12-tetraazadodecane, 1,5,8,12-tetrakis[2,4-bis(N-butyl-N-(1,2,2,6,6-pentamethyl-4-piperidyl)amino)-s-triazine-6-il]-1,5,8,12-tetraazadodecane, 1,6,11-tris[2,4-bis(N-butyl-N-(2,2,6,6-tetramethyl-4-piperidyl)amino)-s-triazine-6-il-amino]undecane and 1,6,11-tris[2,4-bis(N-butyl-N-(1,2,2,6,6-pentamethyl-4-piperidyl) amino)-s-triazine-6-il amino]undecane.

Examples of a nucleating agent are aromatic carboxylic acid metal salts such as aluminum p-t-butyl benzoate and sodium benzoate; acid phosphoric acid ester metal salts such as bis(2,4-di-t-butylphenyl) sodium phosphate, bis(2,4-di-t-butylphenyl) lithium phosphate and sodium-2,2'-methylene bis(4,6-di-t-butylphenyl)phosphate; and polyhydric alcohol derivatives such as dibenzylidene sorbitol and bis(methylbenzylidene) sorbitol.

Examples of a flame retarder are halogen type flame retarders, phosphorus type flame retarders such as red phosphorus, melamine phosphate, piperazine phosphate, guanidine phosphate, melamine pyrophosphate, piperazine pyrophosphate, guanidine pyrophosphate, melamine polyphosphate, melamine polyphosphate, guanidine polyphosphate, phosphoric acid ester compounds and phosphazene compounds, nitrogen type flame retarders such as melamine cyanurate, and metal hydroxides such as magnesium hydroxide and aluminum hydroxide; examples of a flame retarder auxiliary agent are inorganic compounds such as antimony trioxide and zinc borate, and drip inhibitors such as polytetrafluoroethylene.

The hydrotalcite may be a natural product or a synthetic compound, and it may be used regardless of whether or not a surface treatment has been performed, or whether or not it has any water of crystallization. For example, the basic carbonate represented by the following general formula (IV) may be mentioned.

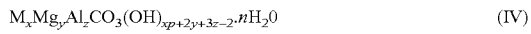   (IV)

(in the formula, M is an alkali metal or zinc, X is a number from 0-6, y is a number from 0-6, z is a number from 0.1-4, p is the valency of M, and n represents the number of molecules of water of crystallization from 0-100.

An example of a lubricant are fatty acid amides such as lauryl amide, myristyl amide, lauryl amide, stearyl amide and behenyl amide, ethylene bis-stearyl amide, polyethylene wax, metal soaps such as calcium stearate and magnesium stearate, and metal salts of phosphoric acid esters such as magnesium distearyl phosphoric acid ester and magnesium stearyl phosphoric acid ester.

Examples of a filler are an inorganic material such as talc, silica, calcium carbonate, glass fiber, potassium titanate, potassium borate, carbon black or carbon fiber, carbon nanoparticles such as fullerene and carbon nanotube. When the inorganic material consists of spherical particles, the particle size may be selected as appropriate. When it consists of fibers, the fiber diameter, fiber length and aspect ratio may be selected as appropriate. The filler may also be given a surface treatment if required.

When the resin composition with which the hindered amine compound of the present invention was blended, is used as an agricultural film, an ultraviolet absorber may be blended therewith to control the growth of crops, an infrared absorption agent may be blended therewith to improve temperature retention properties, and since fogging may occur in a greenhouse, and condensation may form on the film surface which prevents sufficient light from reaching the crops, an anti-clouding agent, anti-misting agent or drop-flowing agent may also be blended therewith.

The hindered amine compound of this invention has the effect of stabilizing a synthetic resin, and in particular, the synthetic resin composition may be used as a polyolefin agricultural film exposed to acidic components by the fumigation of agricultural chemicals or sulfur, a coating material exposed to acid rain outdoors, or a sealant.

The hindered amine compound of the present invention may also be used in applications in which a long-term stabilization effect of an organic substance is required, such as resin compositions having acidic ingredients in which the prior art hindered amine compounds were not fully able to demonstrate a stabilization effect due to the effect of the acidic ingredients such as melamine pyrophosphate, liquid products such as lubricating oils or electrolytic solutions.

EXAMPLES

The invention will now be described in detail referring to specific examples, but the invention is not to be construed as being limited in any way by the following Examples.

Example 1

Synthesis of Compound No. 1

17.0 g (98.1 mmol) of 4-hydroxy-1-oxy-2,2,6,6-tetramethyl piperidine was dissolved in 40.0 g of chlorobenzene, and a solution containing 31.3 g (78.5 mmol) dilauroyl peroxide dissolved in 125 g chlorobenzene was dripped in at 70° C. over 3 hours. The reaction was performed at this temperature for a further 6 hours. The obtained reaction liquid was analyzed by gas chromatography to verify consumption of the starting materials. The obtained reaction liquid was a mixture of 4-hydroxy-1-undecanoxy-2,2,6,6-tetramethyl piperidine, 1-undecanoxy-2,2,6,6-tetramethyl piperidine-4-one, lauric acid and a solvent. 50 g of hexane was added to the reaction liquor, the reaction liquor was washed with 53.9 g (98 mmol) of 7.3% sodium hydroxide aqueous solution and 25 g methanol, washed twice more with 30 g water, and lauric acid was removed. The mixture was dried with anhydrous magnesium sulfate, the magnesium sulfate was removed by filtration, and the solvent was removed under reduced pressure on the evaporator. 70 ml of ethanol was added to the concentrate, and 20 ml of an ethanol solution of 0.57 g (15 mmol) of sodium borohydride was dripped in at room temperature for 20 minutes. The mixture was reacted for a further 1 hour, elimination of 1-undecanoxy-2,2,6,6-tetramethyl piperidine-4-one was verified, the solvent removed under reduced pressure, 50 ml of toluene was added, and the mixture washed 5 times with 30 ml water. Next, water was removed by evaporation under reduced pressure with reflux at 40° C., the solvent was removed under reduced pressure, and 23.0 g of 4-hydroxy-1-undecanoxy-2,2,6,6-tetramethyl piperidine of purity 96.1% as determined by area ratio on the gas chromatograph, was obtained as a colorless liquid (yield 68.8%).

12.0 g (35.17 mmol) of the obtained 4-hydroxy-1-undecanoxy-2,2,6,6-tetramethyl piperidine of purity 96.1%, 4.19 g (19.34 mmol) of diphenyl carbonate and 0.6 g of potassium carbonate were dispersed in 100 ml of mineral spirits, reacted at 170-180° C. for 8 hours, and phenol was removed. The mixture was cooled to 40° C., and washed 3 times with 30 ml water. Water was removed by evaporation under reduced pressure with reflux at 60° C., and the solvent was removed under reduced pressure on the evaporator. The concentrate was purified by silica gel column chromatography (developing solvent: toluene), and bis(1-undecanoxy-2,2,6,6-tetramethyl piperidine-4-il) carbonate (yield 55.5%) of purity 99.9% by the aforesaid analysis method was obtained as a colorless liquid.

The analysis result of the obtained Compound No. 1 is shown below:
IR Spectrum
2800-3050 cm$^{-1}$, 1740 cm$^{-1}$, 1450 cm$^{-1}$, 1380 cm$^{-1}$, 1360 cm$^{-1}$, 1310 cm$^{-1}$, 1270 cm$^{-1}$, 1240 cm$^{-1}$, 1190 cm$^{-1}$, 1000 cm$^{-1}$
$^1$H-NMR spectrum (H: Actual measurement of number of protons, figures in brackets [ ] are calculated values)
δ 0.75-2.05 (H in CH$_3$ and C—CH$_2$—C, 72.8 [74])
δ 3.55-3.85 (H in CH$_2$—O: 4.2 [4])
δ 4.60-5.10 (H in CH—O: 2.0 [2])

Example 2

Synthesis of Compound No. 7

Synthesis of 1-undecaneoxy-2,2,6,6-tetramethyl piperidine-4-one 15.0 g (86.6 mmol) of 4-hydroxy-1-oxy-2,2,6,6-tetramethyl piperidine was dissolved in 40.0 g of chlorobenzene, and a solution containing 27.6 g (69.3 mmol) dilauroyl peroxide dissolved in 125 g chlorobenzene was dripped in at 70° C. over 3 hours. The reaction was performed at this temperature for a further 6 hours. The obtained reaction liquid was analyzed by gas chromatography to verify consumption of the starting materials. 0.1 g of 4-acetyl-1-oxy-2,2,6,6-tetramethyl piperidine was added to the reaction liquor to suppress decomposition reactions, the mixture was cooled to 0° C., and 48.3 g (64.9 mmol) of 10% sodium hypochlorite aqueous solution was dripped in over 3 hours. The reaction was continued for 3 hours at the same temperature, 15 ml of 15 wt % sodium thiosulfate aqueous solution was added, and the mixture was heated to 40° C. and reacted for 1 hour. The organic layer and aqueous layer were separated, the aqueous layer was extracted twice with 70 ml toluene, and the toluene was dehydrated by anhydrous magnesium sulfate together with the organic layer. The magnesium sulfate was filtered off, the filtrate was concentrated under reduced pressure, 50 g hexane was added, 17.3 g (86.6 mmol) of 20% sodium hydroxide aqueous solution was added at 55° C., 15 g methanol was added, and the mixture allowed to stand. The aqueous layer was removed, and washed twice with 15 g water. The water was removed by heating under reflux, the solvent was removed, the mixture dissolved in 40 g methanol, cooled to 40° C., and crystals were deposited. 14.4 g of a white powder of 1-undecyloxy-2,2,6,6-tetramethyl piperidine-4-one was obtained by filtration (yield 50%). It was a colorless liquid at room temperature.

The analysis result of the obtained Compound No. 7 is shown below.

IR Spectrum
2860-3040 $cm^{-1}$, 2360 $cm^{-1}$, 1740 $cm^{-1}$, 1460 $cm^{-1}$, 1360 $cm^{-1}$, 1265 $cm^{-1}$, 1200 $cm^{-1}$, 1100 $cm^{-1}$, 980 $cm^{-1}$ $^1$H-NMR spectrum (H: Actual measurement of number of protons, figures in brackets [ ] are calculated values.)
δ 0.75-2.10 (H in $CH_3$ and C—$CH_2$—C, 85.4 [84])
δ 3.25-4.45 (H in $CH_2$—O: 16.0 [16])

Synthesis of Cyclic-Acetal Skeleton Intermediate

Synthesis Example 1 and Synthesis Example 2

8.00 g (24.58 mmol) of 1-undecanoxy-2,2,6,6-tetramethyl piperidine-4-one, (34.41 mmol) of the polyhydric alcohol shown in TABLE 1, 0.54 g of p-toluene sulfonic acid and 76.00 g cyclohexane were introduced into a flask, 25 g methanol was dripped in at 70-80° C. over 7 hours, and the mixture was kept at the same temperature for a further 2 hours. Methanol and water were distilled off, the mixture was cooled to 40° C., 40 ml of ethyl acetate, 0.15 g of sodium carbonate and 30 ml of water were added, and the mixture stirred for 30 minutes. After standing, the aqueous layer was removed, washed twice more with 20 ml water, the organic layer was dried with anhydrous magnesium sulfate, and the magnesium sulfate was removed by filtration. The filtrate was evaporated under reduced pressure, and a light yellow, viscous liquid was obtained. The obtained liquid was purified by column chromatography (silica gel). TABLE 1 shows the diol used, yield, description and purity measured by liquid chromatography.

The compound obtained in Synthesis Example 1 is an intermediate of Compound No. 7, and the compound obtained in Synthesis Example 2 was used for Example 3 as an intermediate of Compound No. 11.

TABLE 1

| Synthesis Example | Polyvalent alcohol | Yield (%) | Description (Liquid) | Purity (%) |
|---|---|---|---|---|
| 1 | Trimethyloylpropane | 80.6 | Light yellow | 99.9 |
| 2 | Glycerine | 63.7 | Light yellow | 99.9 |

8.10 g (18.4 mmol) of 1,5-dioxa-9-aza-3-ethyl-3-hydroxymethyl-8,8,10,10-tetramethyl-9-undecyloxyspiro[5.5]undecane, 2.16 g (10.1 mmol) diphenyl carbonate and 0.7 g of potassium carbonate were dispersed in 100 ml of mineral spirit, reacted at 170-180° C. for 8 hours, and phenol was removed. The mixture was cooled to 40° C., and washed 3 times with 30 ml water. Water was removed under reduced pressure with reflux at 60° C., and the solvent was removed under reduced pressure on the evaporator. The concentrate was recrystallized from ethanol by cooling to 0° C., and Compound No. 7 of purity 99.3% (yield 39.5%) was obtained as colorless crystals with a melting point of 118.8° C.

Example 3

Synthesis of Compound No. 11

8.0 g (20 mmol) of the 1,5-dioxa-9-aza-3-hydroxy-8,8,10,10-tetramethyl-9-undecyloxyspiro[5.5]undecane obtained in Synthesis Example 2, 2.35 g (11.0 mmol) diphenyl carbonate and 0.7 g potassium carbonate were dispersed in 100 ml mineral spirit, reacted at 170-180° C. for 8 hours, and phenol was removed. The mixture was cooled to 40° C., and washed 3 times with 30 ml water. Water was removed under reduced pressure with reflux at 60° C., and the solvent was removed under reduced pressure on the evaporator. The concentrate was recrystallized from ethanol by cooling to 0° C., and Compound No. 11 of purity 99.9% was obtained as colorless crystals with a melting point of 87.4° C. (yield 68.4%).

The analysis result of the obtained compound No. 11 is shown below.

IR Spectrum
2850-2920 $cm^{-1}$, 1750 $cm^{-1}$, 1470 $cm^{-1}$, 1360 $cm^{-1}$, 1280 $cm^{-1}$, 1230 $cm^{-1}$, 1200 $cm^{-1}$, 1100 $cm^{-1}$, 1030 $cm^{-1}$, 960 $cm^{-1}$.

$^1$H-NMR spectrum (H: Actual measurement of number of protons, figures in brackets [ ] are calculated values.)
δ 0.75-2.05 (H in $CH_3$ and C—$CH_2$—C, 76.2 [74])
δ 3.60-4.70 (H in $CH_2$—O and CH—O: 14.0 [14])

Example 4

Synthesis of Compound No. 13

10.0 g (57.7 mmol) of 4-hydroxy-1-oxy-2,2,6,6-tetramethylpiperidine was dissolved in 40.0 g chlorobenzene, and a solution of 54.4 g (49.1 mmol) distearoyl peroxide dissolved in 200 g chlorobenzene was dripped in at 70° C. over 2 hours. The reaction was continued for a further 3 hours at the same temperature, and the obtained reaction liquor was analyzed by gas chromatography. The area ratio of starting material: stearic acid:target material was 7.8:21.9:70.3. Solvent was removed from the reaction liquor under reduced pressure, 40 g hexane was added, 31.6 g (57.7 mmol) of 7.3% sodium hydroxide aqueous solution and 25 g ethanol were added, the mixture stirred at 40° C. for 30 minutes, washed by oil/water separation, washed twice more with 30 g water, and lauric acid was removed. The mixture was dried with anhydrous magnesium sulfate, the magnesium sulfate was removed by filtration, and the solvent was removed under reduced pressure on the evaporator. 40 ml of ethanol was added to the concentrate, and 0.19 g (5 mmol) of sodium borohydride dissolved in 5 ml ethanol was dripped in at room temperature for 10 minutes. The mixture was reacted for a further 1 hour, elimination of 1-undecanoxy-2,2,6,6-tetramethylpiperidine-4-one was verified, the solvent removed under reduced pressure, 40 ml of toluene was added, and the mixture washed 5 times with 20 ml water. Next, water was removed by evaporation under reduced pressure with reflux at 40° C., the solvent was removed under reduced pressure, the mixture, as 40 ml of an ethanol solution at 40° C., was cooled to 0° C., and 4-hydroxy-1-stearyloxy-2,2,6,6-tetramethylpiperidine of purity 94.0% as determined by area ratio on the gas chromatograph, was obtained as white crystals (yield 26.4%).

8.70 g (19.9 mmol) of the obtained 4-hydroxy-1-stearyloxy-2,2,6,6-tetramethylpiperidine, 2.15 g (9.90 mmol) of diphenyl carbonate and 0.2 g of potassium carbonate were dispersed in 60 ml of mineral spirits, reacted at 170-180° C. for 6 hours, and phenol was removed. The mixture was cooled to 50° C., and washed 3 times with 30 ml water. Water was removed by evaporation under reduced pressure with reflux at 60° C., and the solvent was removed under reduced pressure on the evaporator. The concentrate was crystallized from a mixed solvent (toluene/ethanol=2:8 (volume ratio)), and bis(1-stearyloxy-2,2,6,6-tetramethylpiperidine-4-il) carbonate (yield 73.8%) of purity 99.9% was obtained as a white powder of melting point 52° C.

Examples 5-7 and Comparative Examples 1-4

Polyethylene Composition 0.05 weight parts of calcium stearate, 0.05 weight parts of tetrakis(3-(3,5-di-t-butyl-4-hydroxyphenyl) propionyloxymethyl)methane, 0.05 weight parts of tris(2,4-di-t-butylphenyl) phosphite and the hindered amine compound shown in TABLE 2 (weight parts) were added to 100 weight parts of linear low-density polyethylene resin (Produced by Nippon Unica Co., Ltd.: PES120), and pelletized by a single screw extruder at a cylinder temperature of 200° C. and screw rotation speed of 25 rpm. The obtained pellets were pressed at 180° C. to form a film of thickness 80 nm.

The obtained film was placed in a 1 m×1 m×1 m corrugated paper container, fumigated with 2 g of sulfur by a hot plate, left for 24 hours, and the carbonyl index was measured after exposure of 600 hours with a Sunshine Weather Meter at 63° C. under rainy conditions. Here, the carbonyl index is defined by $[\log(I_o/I)]/d$ using the infrared absorption spectrum analysis data for the film. Here, Io is the transmissivity (%) before deterioration at 1710 $cm^{-1}$, I is the transmissivity (%) after deterioration, and d is the film thickness (cm). The higher the numerical value, the more the film has deteriorated. TABLE 2 shows the results.

(a) in TABLE 2 means that measurement was impossible since deterioration was too severe.

TABLE 2

| | Hindered amine compound | Blending amount | Carbonyl index |
|---|---|---|---|
| Example | | | |
| 5 | Compound No. 1 | 0.5 | 0.06 |
| 6 | Compound No. 7 | 0.5 | 0.30 |
| 7 | Compound No. 11 | 0.5 | 0.28 |
| Comparative Example 1 | None | — | 0.59 |
| Comparative Example 2 | Comparison compound 1*[1] | 0.5 | 0.47 |
| Comparative Example 3 | Comparison compound 2*[2] | 0.5 | (a) |
| Comparative Example 4 | Comparison compound 3*[3] | 0.5 | 0.77 |

*[1]:
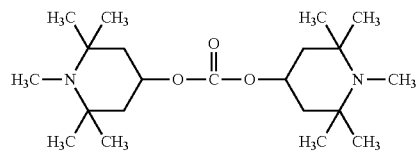

*[2]:
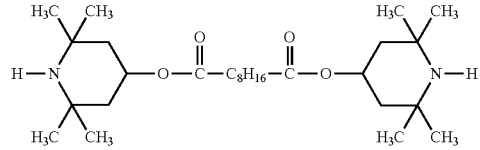

*[3]:
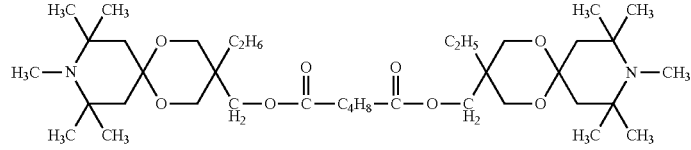

Example 8 and Comparative Example 5

0.5 weight parts of the hindered amine compound in Table 3 was added to 100 weight parts of an organic solvent type acrylic coating (Mr. Color Super Clear: Produced by GSI Creos Co.), the mixture was coated on an aluminum substrate having a film thickness of 50-60 μm, and the gloss retention factor and color difference were measured after 500 hours exposure by a Xenon Weather Meter at 63° C. under rainy conditions (18 minutes spraying with water in 120 minutes). TABLE 3 shows the results.

TABLE 3

|  | Hindered amine compound | Gloss retention (%) | Color difference |
| --- | --- | --- | --- |
| Example 8-1 | Compound No. 1 | 94 | 6.79 |
| Comparative Example 5-1 | None | 95 | 8.61 |
| Comparative Example 5-2 | Comparison compound 4 *[4] | 94 | 10.62 |

*[4]:

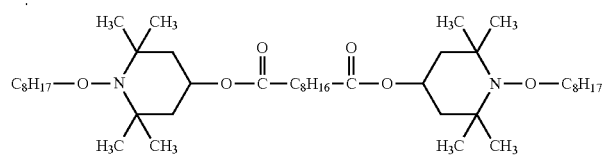

Example 9 and Comparative Example 6

72 weight parts of a phthalic acid plasticizer (Adeka Sizer DL-911P), 10 weight parts of tricresylphospate, 3 weight parts of epoxidized soybean oil, 2.5 weight parts of a Ca/Zn liquefied stabilizer (Adeka Stub AC-212: Asahi Denka Kogyo K. K.), 0.5 weight parts of CPL-46 (liquefied perchlorate stabilizer (Adeka Stub CPL-46)), 0.83 weight parts of liquefied phosphorous acid ester stabilizer (Adeka Stub 1500: Asahi Denka Kogyo K.K.) and 0.17 weight parts of the hindered amine compound shown in TABLE 4, were blended with 100 weight parts of vinyl chloride resin (TK-1300: Shin-Etsu Chemical Industries Co., Ltd), and roll-worked into a sheet of thickness 1 mm. The weather resistance of the obtained sheet was evaluated from the color change to blackish brown by a Fade Meter at 83° C. TABLE 4 shows the results.

TABLE 4

|  | Hindered amine compound | Weatherability (hours) |
| --- | --- | --- |
| Example 9-1 | Compound No. 1 | 1250 |
| Comparative Example 6-1 | Comparison compound 2 *[2] | 500 |
| Comparative Example 6-2 | Comparison compound 4 *[4] | 1000 |

Example 10 and Comparative Example 7

80 weight parts of a block polypropylene (MFR=25 g/10 minutes, density=0.9 g/cm$^3$, bending elastic modulus 950 MPa), 20 weight parts of melamine pyrophosphate, 0.1 weight parts of calcium stearate, 0.1 weight parts of tetrakis(3-(3,5-di-t-butyl-4-hydroxyphenyl) propionyloxymethyl) methane, 0.1 weight parts of tris(2,4-di-t-butylphenyl)phosphite, 0.2 weight parts of polytetrafluoroethylene and 0.2 weight parts of the hindered amine compound in TABLE 5 were mixed together, and pelletized by a single screw extruder at a cylinder temperature of 230° C., and screw rotation speed of 25 rpm. The obtained pellets were injection molded at 230° C., and evaluated by a Sunshine Weather Meter at 63° C. under rainy conditions (18 minutes spraying with water in 120 minutes), and with no rain at 83° C. TABLE 5 shows the results.

TABLE 5

|  | Hindered amine compound | Weatherability: with rain (hours) | Weatherability: no rain (hours) |
| --- | --- | --- | --- |
| Example 10-1 | Compound No. 1 | 3480 | 960 |
| Comparative Example 7-1 | None | 240 | 120 |
| Comparative Example 7-2 | Comparison compound 4 *[4] | 2160 | 720 |

Example 11 and Comparative Example 8

100 weight parts of a block polypropylene (MFR=25 g/10 minutes, density=0.9 g/cm$^3$, bending elastic modulus 950 MPa), 0.1 weight parts of calcium stearate, 0.1 weight parts of tetrakis(3-(3,5-di-t-butyl-4-hydroxyphenyl) propionyloxymethyl)methane, 0.1 weight parts of tris(2,4-di-t-butylphenyl) phosphite and 0.2 weight parts of the hindered amine compound in TABLE 6 were extruded into pellets at 250° C., and injection molded at 250° C. into a test piece of thickness 2 mm. The coloring properties were evaluated from the degree of yellowing of the obtained test piece, and weatherability was evaluated by a Sunshine Weather Meter at 83° C. with no rain from the time until cracks appeared.

TABLE 6

|  | Hindered amine compound | Heat resistance (degree of yellowing) | Weatherability, no rain (hours) |
| --- | --- | --- | --- |
| Example 11-1 | Compound No. 1 | 6 | 1680 |
| Comparative Example 8-1 | None | 6 | 240 |
| Comparative Example 8-2 | Comparison compound 4 *[4] | 8.5 | 1320 |

INDUSTRIAL APPLICABILITY

Due to the present invention, a hindered amine compound which imparts long-term weather resistance can be provided. Also, a synthetic resin composition having superior long-term weather resistance, and in particular, a polyolefin resin composition suitable for agricultural films can be provided.

What is claimed is:

1. A synthetic resin composition, comprising 100 weight parts of a synthetic resin and 0.01 to 10 weight parts of a hindered amine compound of formula I

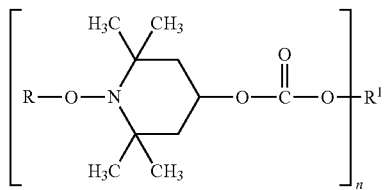

wherein R in formula I is an alkyl group or a hydroxyalkyl group having 1-30 carbon atoms, and when n=1, $R^1$ is an alkyl group having 1-22 carbon atoms, an alkenyl group having 2-22 carbon atoms, or a group of formula (III):

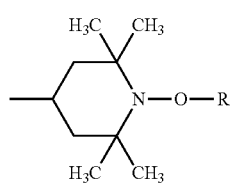

wherein R in formula III is an alkyl group or hydroxyalkyl group having 1-30 carbon atoms, when n=2-6, $R^1$ is an organic group having 2-20 carbon atoms of valency n and wherein R in formula I may be the same as or different from R in formula III.

2. The synthetic resin composition according to claim 1, further comprising 1-30 weight parts of one or more of melamine phosphate, melamine pyrophosphate, melamine polyphosphate, piperazine phosphate, piperazine pyrophosphate or piperazine polyphosphate as a flame retarder.

3. The synthetic resin composition according to claim 1, wherein
n=2,
R in formula I is an alkyl group having 4-22 carbon atoms and
$R^1$ is an alkyne group having 2-12 carbon atoms.

4. The synthetic resin composition according to claim 1, wherein
n=1,
R in formula I is an alkyl group having 10-22 carbon atoms, $R^1$ is the group of formula III and
R in formula III is an alkyl group having 10-22 carbon atoms.

5. The synthetic resin composition according to claim 1, wherein R in formula (I) or R in formula (III) is methyl, ethyl, propyl, isopropyl, butyl, isobutyl, sec-butyl, tert-butyl, pentyl, sec-pentyl, tert-pentyl, hexyl, heptyl, octyl, iso-octyl, 2-ethylhexyl, tert-octyl, nonyl, isononyl, decyl, undecyl, dodecyl, tridecyl, tetradecyl, pentadecyl, hexadecyl, heptadecyl or octadecyl.

6. The synthetic resin composition according to claim 1, wherein R in formula (I) or R in formula (III) is a cycloalkyl.

7. The synthetic resin composition according to claim 1, wherein R in formula (I) or R in formula (III) is 2-hydroxyethyl, 2-hydroxypropyl, 2-hydroxybutyl or 2-hydroxy-2-methylpropyl.

8. The synthetic resin composition according to claim 1, further comprising 0.001-10 weight parts of a phenol type antioxidant, a sulfur type antioxidant or a phosphorus type antioxidant.

9. The synthetic resin composition according to claim 8, wherein said phenol type antioxidant is α-tocopherol, 2,6-di-t-butyl-p-cresol, 2,6-diphenyl-4-octadecyloxyphenol, distearyl(3,5-di-t-butyl-4-hydroxybenzyl)phosphonate, 1,6-hexamethylene bis[(3,5-di-t-butyl-4-hydroxyphenyl) propionic acid amide], 4,4'-thiobis(6-t-butyl-m-cresol), 2,2'-methylene bis(4-methyl-6-t-butylphenol), 2,2'-methylene bis(4-ethyl-6-t-butylphenol), 4,4'-butylidene bis(6-t-butyl-m-cresol), 2,2'-ethylidene bis(4,6-di-t-butylphenol), 2,2'-ethylidene bis(4-s-butyl-6-t-butylphenol), 1,1,3-tris(2-methyl-4-hydroxy-5-t-butylphenyl)butane, 1,3,5-tris(2,6-dimethyl-3-hydroxy-4-t-butylbenzyl)isocyanurate, 1,3,5-tris (3,5-di-t-butyl-4-hydroxybenzyl)isocyanurate, 1,3,5-tris(3, 5-di-t-butyl-4-hydroxybenzyl)-2,4,6-trimethylbenzene, 2-t-butyl-4-methyl-6-(2-acryloyloxy-3-t-butyl-5-methylbenzyl) phenol, stearyl(3,5-di-t-butyl-4-hydroxyphenyl) propionate, thiodiethyleneglycol bis[(3,5-di-t-butyl-4-hydroxyphenyl) propionate], 1,6-hexamethylene bis-(3,5-di-t-butyl-4-hydroxyphenyl)propionate], bis[3,3-bis(4-hydroxy-3-t-butylphenyl)butyric acid]glycolester, bis[2-t-butyl-4-methyl-6-(2-hydroxy-3-t-butyl-5-methylbenzyl)phenyl]terephthalate, 1,3,5-tris[(3,5-di-t-butyl-4-hydroxyphenyl)propionyloxyethyl]isocyanurate, 3,9-bis[1,1-dimethyl-2{(3-t-butyl-4-hydroxy-5-methylphenyl)propionyloxy}ethyl]2,4,8,10-tetraoxaspiro[5.5]undecane or triethyleneglycol bis[(3-t-butyl-4-hydroxy-5-methylphenyl) propionate].

10. The synthetic resin composition according to claim 8, wherein said sulfur type antioxidant is dilauryl thiodipropionate, dimyristyl thiodipropionate, distearyl thiodipropionate, or pentaerythritol tetra(β-dodecyl mercaptopropionate).

11. The synthetic resin composition according to claim 8, wherein said phosphorus type antioxidant is tris-nonyl phenylphosphite, tris[2-t-butyl-4-(3-t-butyl-4-hydroxy-5-methylphenylthio)-5-methylphenyl]phosphite, tridecyl phosphite, octyl diphenyl phosphite, di(decyl)monophenyl phosphite, di(tridecyl)pentaerythritol diphosphite, di(nonylphenyl)pentaerythritol diphosphite, bis(2,4-di-t-butylphenyl)pentaerythritol diphosphite, bis(2,6-di-t-butyl-4-methylphenyl) pentaerythritol diphosphite, bis(2,4,6-tri-t-butylphenyl) pentaerythritol diphosphite, bis(2,4-dicumylphenyl) pentaerythritoldiphosphite, tetra(tridecyl) isopropylidene diphenoldiphosphite, tetra(tridecyl)-4,4'-n-butylidene bis(2-t-butyl-5-methylphenol)diphosphite, hexa(tridecyl)-1,1,3-tris(2-methyl-4-hydroxy-5-t-butylphenyl)butanetriphosphite, tetrakis(2,4-di-t-butylphenyl)biphenylene diphosphonite, 9,10-dihydro-9-oxa-10-phosphaphenanthrene-10-oxide, 2,2'-methylene bis(4,6-t-butylphenyl)-2-ethylhexylphosphite, 2,2'-methylene bis(4,6-t-butylphenyl)-octadecylphosphite, 2,2'-ethylidene bis(4,6-di-t-butylphenyl)fluorophosphite, tris(2-[(2,4,8,10-tetrakis-t-butyldibenzo[d,f][1,3,2]dioxaphosphepine-6-il)oxy]ethyl) amine, or the phosphites of 2-ethyl-2-butyl propyleneglycol and 2,4,6-tri-t-butylphenol.

12. A polyolefin resin composition, comprising 100 weight parts of a polyolefin resin and 0.05-5 weight parts of the hindered amine compound of formula I

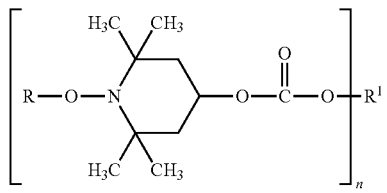
(I)

wherein R in formula I is an alkyl group or a hydroxyalkyl group having 1-30 carbon atoms, and when n=1, $R^1$ is an alkyl group having 1-22 carbon atoms, an alkenyl group having 2-22 carbon atoms, or a group of formula (III):

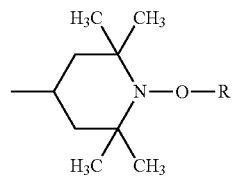
(III)

wherein R in formula III is an alkyl group or hydroxyalkyl group having 1-30 carbon atoms,
when n=2-6, $R^1$ is an organic group having 2-20 carbon atoms of valency n and
wherein R in formula I may be the same as or different from R in formula III.

13. An agricultural polyolefin film comprising the polyolefin resin composition according to claim 12.

* * * * *